(12) United States Patent
Brousseau, III (10) Patent No.: US 6,784,082 B2
(45) Date of Patent: Aug. 31, 2004

(54) METHODS OF FABRICATING SINGLE ELECTRON TRANSISTORS IN WHICH THE THICKNESS OF AN INSULATING LAYER DEFINES SPACING BETWEEN ELECTRODES

(75) Inventor: Louis C. Brousseau, III, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/244,860

(22) Filed: Sep. 17, 2002

(65) Prior Publication Data

US 2003/0025133 A1 Feb. 6, 2003

Related U.S. Application Data

(62) Division of application No. 09/905,319, filed on Jul. 13, 2001, now Pat. No. 6,483,125.

(51) Int. Cl.$^7$ ............................................... H01L 21/20
(52) U.S. Cl. ...................... 438/584; 438/483; 438/618; 438/702; 438/780
(58) Field of Search .............................. 438/584, 618, 438/758, 780, 172, 483, 702

(56) References Cited

U.S. PATENT DOCUMENTS

| | | | |
|---|---|---|---|
| 4,777,019 A | 10/1988 | Dandekar | 422/68 |
| 4,778,769 A | 10/1988 | Forrest et al. | 436/501 |
| 4,877,582 A | 10/1989 | Oda et al. | 422/68 |

(List continued on next page.)

FOREIGN PATENT DOCUMENTS

| | | |
|---|---|---|
| EP | 0 884 768 A2 | 12/1998 |
| WO | WO 93/08464 | 4/1993 |
| WO | WO 99/61911 | 12/1999 |
| WO | WO 01/13432 | 2/2001 |

OTHER PUBLICATIONS

International Search Report, PCT/US/22747, Dec. 21, 2000.
Dziuban et al., *Mold–Type Field–Emission Array Fabrication by the Use of Fast Silicon Etching*, J. Vac. Sci. Technol. B, vol. 19, No. 3, May/Jun. 2001, pp. 897–899.
Rangelow et al., *Fabrication and Electrical Characterization of High Aspect Ratio Silicon Field Emitter Arrays*, J. Vac. Sci. Technol. B, vol. 19, No. 3, May/Jun. 2001, pp. 916–919.
Lenigk et al., *Surface Characterization of a Silicon–Chip–Based DNA Microarray*, Langmuir, 2001, pp. 2497–2501.

(List continued on next page.)

*Primary Examiner*—Thanh Nguyen
(74) *Attorney, Agent, or Firm*—Myers Bigel Sibley & Sajovec (57) ABSTRACT

Single-electron transistors include first and second electrodes and an insulating layer between them on a substrate. The insulating layer has a thickness that defines a spacing between the first and second electrodes. At least one nanoparticle is provided on the insulating layer. Accordingly, a desired spacing between the first and second electrodes may be obtained without the need for high resolution photolithography. An electrically-gated single-electron transistor may be formed, wherein a gate electrode is provided on the at least nanoparticle opposite the insulating layer end. Alternatively, a chemically-gated single-electron transistor may be formed by providing an analyte-specific binding agent on a surface of the at least one nanoparticle. Arrays of single-electron transistors also may be formed on the substrate. The single-electron transistors may be fabricated by forming a post electrode on a substrate, conformally forming an insulating layer on at least a portion of the post electrode and conformally forming a second electrode on at least a portion of the insulating layer opposite the post electrode. At least one nanoparticle is placed on the insulating layer, between the post electrode and the second electrode.

25 Claims, 7 Drawing Sheets

U.S. PATENT DOCUMENTS

| | | | | |
|---|---|---|---|---|
| 4,894,339 | A | 1/1990 | Hanazato et al. | 435/182 |
| 5,039,390 | A | 8/1991 | Hampp et al. | 204/412 |
| 5,219,577 | A | 6/1993 | Kossovsky et al. | 424/494 |
| 5,420,746 | A | 5/1995 | Smith | 361/311 |
| 5,543,351 | A | 8/1996 | Hirai et al. | |
| 5,576,563 | A | 11/1996 | Chung | 257/253 |
| 5,646,420 | A | 7/1997 | Yamashita | 257/17 |
| 5,653,939 | A | 8/1997 | Hollis et al. | 422/50 |
| 5,747,839 | A | 5/1998 | Hammond et al. | 257/253 |
| 5,828,076 | A | 10/1998 | Gossner et al. | |
| 5,844,834 | A | 12/1998 | Risch et al. | 365/150 |
| 5,892,252 | A | 4/1999 | Hammond et al. | 257/252 |
| 5,899,734 | A | 5/1999 | Lee et al. | 438/584 |
| 5,900,728 | A | 5/1999 | Moser et al. | 324/244 |
| 5,900,729 | A | 5/1999 | Moser et al. | 324/244 |
| 5,922,537 | A | 7/1999 | Ewart et al. | 435/6 |
| 5,989,947 | A | 11/1999 | Dilger et al. | 438/172 |
| 5,997,958 | A | 12/1999 | Sato et al. | 427/468 |
| 6,057,556 | A | 5/2000 | Gubin et al. | 257/39 |
| 6,066,265 | A | 5/2000 | Galvin et al. | 216/2 |
| 6,103,868 | A | 8/2000 | Heath et al. | 538/482 |
| 6,121,075 | A | 9/2000 | Yamashita | 438/149 |
| 6,159,620 | A | 12/2000 | Heath et al. | 428/615 |
| 6,211,530 | B1 | 4/2001 | Goronkin et al. | |
| 6,403,321 | B1 * | 6/2002 | Saraf et al. | 435/6 |
| 6,410,934 | B1 * | 6/2002 | Nayfeh et al. | 257/14 |

OTHER PUBLICATIONS

Letsinger et al., *Use of a Steroid Cyclic Disulfide Anchor in Constructing Gold Nanoparticle–Oligonucleotide Conjugates*, Bioconjugate Chem., 2000, vol. 11, pp. 289–291.

Taylor et al., *Probing Specific Sequences on Single DNA Molecules With Bioconjugated Fluorescent Nanoparticles*, Analytical Chemistry, vol. 72, No. 9, May 1, 2000, pp. 1979–1986.

Chan et al., *Quantum Dot Bioconjugates for Ultrasensitive Nonisotopic Detection*, Science, vol. 281, Sep. 25, 1998, pp. 2016–2018.

Bruchez, Jr. et al., *Semiconductor Nanocrystals as Fluorescent Biological Labels*, Science, vol. 281, Sep. 25, 1998, pp. 2013–2016.

Brousseau, III et al., *pH–Gated Single–Electron Tunneling in Chemically Modified Gold Nanoclusters*, Journal of the American Chemical Society, vol. 120, No. 30, 1998, pp. 7645–7646.

Feldheim et al., *Self–Assembly of Single Electron Transistors and Related Devices*, Chemical Society Reviews, vol. 27, 1998, pp. 1–12.

Klein et al., entitled *A Single–Electron Transistor Made From a Cadmium Selenide Nanocrystal*, Nature, 1997, pp. 699–701.

Elghanian et al., *Selective Colorimetric Detection of Polynucleotides Based on the Distance–Dependent Optical Properties of Gold Nanoparticles*, Science, vol. 277, Aug. 22, 1997, pp. 1078–1081.

Yoo et al., *Scanning Single–Electron Transistor Microscopy: Imaging Individual Charges*, Science, vol. 276, Apr. 25, 1997, pp. 579–582.

Abstract, Andres et al., *"Coulomb Staircase" Single Electron Tunneling at Room Temperature in a Self Assembled Molecular Nanostructure*, Science, 1996, vol. 272, pp. 1323–1325.

Ulman, entitled *Formation and Structure of Self–Assembled Monolayers*, Chemical Review, 1996, pp. 1533–1554.

International Search Report, PCT/US02/22137, Feb. 3, 2003.

Takahashi et al., *A Directional Current Switch Using Silicon Single Electron Transistors Controlled by Charge Injection into Silicon Nano–Crystal Floating Dots*, Electron Devices Meeting, 1999, IEDM Technical Digest, pp. 371–374.

* cited by examiner

FIG. 11I

METHODS OF FABRICATING SINGLE ELECTRON TRANSISTORS IN WHICH THE THICKNESS OF AN INSULATING LAYER DEFINES SPACING BETWEEN ELECTRODES

CROSS-REFERENCE TO RELATED APPLICATION

This application is a divisional of application Ser. No. 09/905,319, filed Jul. 13, 2001 (now U.S. Pat. No. 6,483, 125), entitled Single Electron Transistors and Fabrication Methods in Which the Thickness of an Insulating Layer Defines Spacing Between Electrodes, assigned to the assignee of the present application, the disclosure of which is hereby incorporated herein by reference in its entirety as if set forth fully herein.

FIELD OF THE INVENTION

This invention relates to microelectronic devices and fabrication methods therefor, and more particularly to single-electron transistors and fabrication methods therefor.

BACKGROUND OF THE INVENTION

Single-electron Transistor (SET) devices and fabrication methods are being widely investigated for high density and/or high performance microelectronic devices. As is well known to those having skill in the art, single-electron transistors use single-electron nanoelectronics that can operate based on the flow of single-electrons through nanometer-sized particles, also referred to as nanoparticles, nanoclusters or quantum dots. Although a single-electron transistor can be similar in general principle to a conventional Field Effect Transistor (FET), such as a conventional Metal Oxide Semiconductor FET (MOSFET), in a single-electron transistor, transfer of electrons may take place based on the tunneling of single-electrons through the nanoparticles. Single-electron transistors are described, for example, in U.S. Pat. Nos. 5,420,746; 5,646,420; 5,844,834; 6,057,556 and 6,159,620, and in publications by the present inventor Brousseau, III et al., entitled *pH-Gated Single-Electron Tunneling in Chemically Modified Gold Nanoclusters*, Journal of the American Chemical Society, Vol. 120, No. 30, 1998, pp. 7645–7646, and by Feldheim et al., entitled *Self-Assembly of Single Electron Transistors and Related Devices*, Chemical Society Reviews, Vol. 27, 1998, pp. 1–12, and in a publication by Klein et al., entitled *A Single-Electron Transistor Made From a Cadmium Selenide Nanocrystal*, Nature, 1997, pp. 699–701, the disclosures of which are hereby incorporated herein by reference in their entirety as if set forth fully herein.

A major breakthrough in single-electron transistor technology is described in U.S. patent application Ser. No. 09/376,695, entitled *Sensing Devices Using Chemically-Gated Single Electron Transistors*, by Daniel L. Feldheim and the present inventor Louis C. Brousseau, III, also published as International Publication No. WO 01/13432 A1, the disclosures of which are hereby incorporated herein by reference in their entirety as if set fully herein. Described therein is a chemically-gated single-electron transistor that can be adapted for use as a chemical or biological sensor. Embodiments of these chemically-gated single-electron transistors include source and drain electrodes on a substrate and a nanoparticle between the source and drain electrodes, that has a spatial dimension of a magnitude of approximately 12 nm or less. An analyte-specific binding agent is disposed on a surface of the nanoparticle. A binding event occurring between a target analyte and the binding agent causes a detectable change in the characteristics of the single-electron transistor.

Notwithstanding these and other configurations of single-electron transistors, including chemically-gated single-electron transistors, it may be difficult to fabricate these devices using conventional photolithography that is employed to fabricate microelectronic devices. In particular, in order to provide quantum mechanical effects with nanoparticles, it may be desirable to provide spacing between the source and drain electrodes of a single-electron transistor that is less than about 20 nm, or less than about 12 nm or about 10 nm. It may be difficult, however, to provide these spacings using conventional lithography at low cost and/or with acceptable device yields.

SUMMARY OF THE INVENTION

Embodiments of the present invention provide single-electron transistors and manufacturing methods therefor, in which first and second electrodes and an insulating layer therebetween are provided on a substrate. The insulating layer has a thickness that defines a spacing between the first and second electrodes. At least one nanoparticle is provided on the insulating layer. Accordingly, a desired spacing between the first and second electrodes may be obtained without the need for high resolution photolithography.

Embodiments of the present invention may stem from a realization that thin film insulating layers, such as insulating layers that are about 10 nm thick, can be fabricated using conventional microelectronic fabrication techniques, such as chemical vapor deposition, whereas it may be difficult to photolithographically define a region in a layer that is, for example, 10 nm wide. According to embodiments of the invention, single-electron structures and fabrication methods may be provided that allow the thickness of an insulating layer between first and second electrodes to determine spacing between the first and second electrodes. Accordingly, single-electron transistor devices may be fabricated using conventional microelectronic techniques with the potential of low cost and/or high yields.

Single-electron transistors according to embodiments of the present invention comprise a substrate including a face. A first electrode extends from the face, and includes a first electrode end and a sidewall. In some embodiments, the first electrode end is remote from the face, and the sidewall extends between the face and the first electrode. The first electrode may be regarded as a post, tower, mesa, tip, pyramid or cone electrode. An insulating layer is provided on the sidewall, the insulating layer including an insulating layer end that is remote from the face. A second electrode is provided on the insulating layer opposite the sidewall. The second electrode includes a second electrode end. At least one nanoparticle is provided on the insulating layer end. In some embodiments, the insulating layer is less than about 20 nm thick. In other embodiments, the insulating layer is less than about 12 nm thick, and in other embodiments the insulating layer is about 10 nm thick.

In some embodiments of the present invention, the insulating layer end is a continuous insulating layer end that surrounds the sidewall. In other embodiments, the second electrode end is a continuous second electrode end that surrounds the continuous insulating layer end. In yet other embodiments, the continuous insulating layer end and the continuous second electrode end form first and second rings, respectively, that surround the first electrode end. In still other embodiments, the first and second rings are circular, elliptical and/or polygonal first and second rings. In yet other embodiments, the first electrode insulating end and the second electrode insulating end are coplanar.

In some embodiments, the at least one nanoparticle on the insulating layer end comprises a plurality of nanoparticles on the insulating layer end, wherein the first electrode end and the second electrode end are free of nanoparticles thereon. In other embodiments, nanoparticles also are included on the first electrode end and/or on the second electrode end.

In yet other embodiments, a self-assembled monolayer is provided on the insulating layer end, wherein the at least one nanoparticle is on the self-assembled monolayer, opposite the insulating layer end. In still other embodiments, the self-assembled monolayer also is provided on the first electrode end and/or on the second electrode end.

Embodiments of the invention as described above may be used to form an electrically-gated single-electron transistor, wherein a gate electrode is provided on the at least one nanoparticle opposite the insulating layer end. In other embodiments, a chemically-gated single-electron transistor may be provided by providing an analyte-specific binding agent on a surface of the at least one nanoparticle. Moreover, in any of the above embodiments, arrays of single-electron transistors may be formed on the substrate, wherein an array of first electrodes may be provided on the substrate, portions of a single insulating layer may provide the insulating layers on the array of first electrodes and portions of a single conductive layer may provide an array of second electrodes on the array of first electrodes.

Single-electron transistors may be fabricated, according to embodiments of the present invention, by forming a first electrode on a substrate, conformally forming an insulating layer on at least a portion of the first electrode and conformally forming a second electrode on at least a portion of the insulating layer opposite the first electrode. At least one nanoparticle is placed on the insulating layer, between the first electrode and the second electrode.

In some method embodiments, the first electrode is formed by forming a mask region on the substrate and anisotropically etching the substrate with the mask region thereon, to form the first electrode on the first substrate having a first electrode end, with the mask region on the first electrode end. In some embodiments, the insulator is conformally formed on the first electrode, except for the first electrode end that has the mask region thereon and the second electrode is conformally formed on the insulating layer, except for the first electrode end that has the mask region thereon. Moreover, in other embodiments, the mask region is removed from the first electrode end prior to placing the nanoparticle. The nanoparticle is placed on the insulating layer adjacent the first electrode end.

In other method embodiments, the second electrode and the insulating layer are removed from the first electrode end prior to placing the at least one nanoparticle on the insulating layer. The second electrode and the insulating layer may be removed from the first electrode end by forming a recessed layer on the substrate, such that the first electrode end, the insulating layer on the first electrode end and the second electrode on the first electrode end protrude from the recessed layer. The first electrode, the insulating layer on the first electrode end and the second electrode layer on the first electrode end that protrude from the recessed layer are then planarized. Accordingly, the thickness of the insulating layer may determine the spacing between the first and second electrodes, to thereby allow a single-electron transistor to be fabricated using conventional microelectronic processing steps, while allowing high performance and/or high yields.

DETAILED DESCRIPTION OF PREFERRED EMBODIMENTS

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions may be exaggerated for clarity. Like numbers refer to like elements throughout.

Figure 1A:
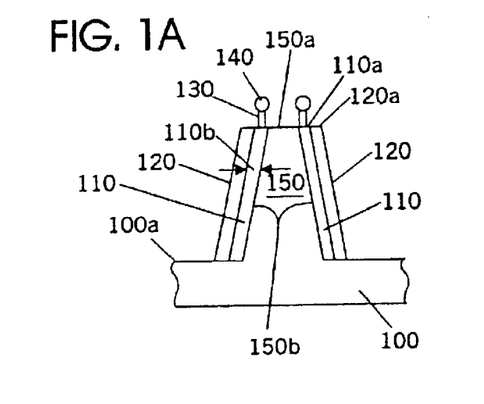
FIGS. 1A, 2A and 3–9 are side cross-sectional views of single-electron transistors according to embodiments of the present invention.
Figure 1B:
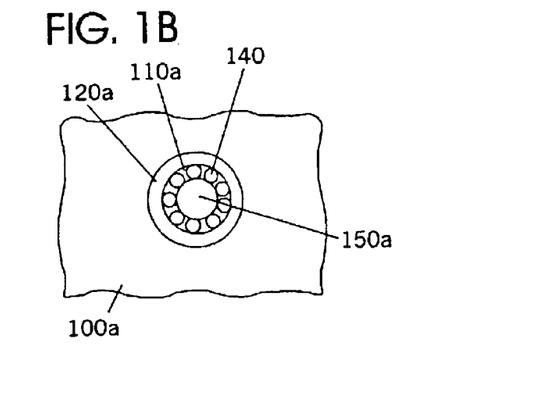
FIGS. 1B–1D and 2B–2D are top views of single-electron transistors according to embodiments of the present invention.

FIGS. 1A and 1B are a side cross-sectional view and a top view, respectively, of single-electron transistors according to embodiments of the present invention. As shown in FIGS. 1A and 1B, these embodiments of single-electron transistors include a substrate 100 including a face 100a. As is well known to those having skill in the art, the substrate can comprise a conventional monocrystalline silicon substrate, a semiconductor-on-insulator (SOI) substrate, a silicon carbide, gallium arsenide, gallium nitride, diamond thin film and/or other substrate, and may also include one or more heteroepitaxial and/or homoepitaxial layers on the substrate. The substrate face 100a may be planar, or non-planar (three-dimensional).

Still referring to FIGS. 1A and 1B, a first electrode 150 is provided that extends from the face. The first electrode 150 includes a first electrode end 150a that is illustrated in FIG. 1A as being remote from the face 100a and a sidewall 150b. In FIG. 1A, the sidewall 150b extends between the face 100a and the first electrode end 150a. Embodiments of the first electrode 150 may be regarded as a post, tower, mesa, tip, pyramid or cone electrode. It will be understood that the first electrode 150 may be conductive or may include a portion thereof that is conductive at least adjacent the end 150a thereof. The first electrode 150 may comprise any of the materials that were described above for the substrate 100, and may also include other conductive materials, such as conductive polysilicon, metal and/or other conductive materials. Although the first electrode 150 is illustrated in FIG. 1A as extending orthogonal to the substrate 100, it also may be oblique or parallel thereto. Moreover, although the sidewall 150b is illustrated as forming an obtuse angle with the face 100a, it may also form a right angle or an acute angle. The sidewall 150b also need not be linear.

Still referring to FIGS. 1A and 1B, an insulating layer 110 is provided on the sidewall 150b. The insulating layer 110 includes an insulating layer end 110a that is remote from the face 100. The insulating layer 110 preferably is a layer of silicon dioxide, silicon nitride, high dielectric constant material and/or other dielectric materials, or multiple sublayers thereof, that can be formed using conventional microelectronic processes, such as Plasma-Enhanced Chemical Vapor Deposition (PECVD), so that the insulating layer 110 may be made relatively thin with high controllability and reliability. More specifically, the thickness 110b of the insulating layer 110 may be less than about 20 nm thick, or less than about 12 nm thick, or about 10 nm thick. The formation of conformal insulating layers on microelectronic substrates is well known to those having skill in the art and need not be described further herein. For example, thin insulators are conventionally used to form the gate insulating layer of MOSFETs. In other embodiments, the insulating layer 110 can include one or more self-assembled monolayers and/or polymer films.

Still referring to FIGS. 1A and 1B, a second electrode 120 is provided on the insulating layer 110 opposite the sidewall 150b. The second electrode 120 includes a second electrode end 120a. The second electrode 120 can comprise a layer or multiple sublayers comprising metal, doped polysilicon and/or other conventional conductive materials, and may be deposited conformally using conventional deposition or other techniques. The deposition of conformal metal layers on microelectronic substrates is well known to those having skill in the art and need not be described further herein. For example, conformal metal layers are conventionally used for electrodes and wiring layers of MOSFETs.

Finally, referring to FIGS. 1A and 1B, at least one nanoparticle 140 is provided on the insulating layer end 110a. The fabrication of at least one nanoparticle 140 on an insulating layer is described, for example, in the above-incorporated Brousseau et al., Feldheim et al. and Klein et al. publications, and need not be described further herein.

In some embodiments, as shown in FIGS. 1A and 1B, a self-assembled monolayer 130 is provided between the at least one nanoparticle 140 and the insulating layer end 110a. Chemical interactions can be used to anchor a nanoparticle on a surface, for example, pursuant to the techniques that are described in a publication to Ulman, entitled *Formation and Structure of Self-Assembled Monolayers*, Chemical Review, 1996, pp. 1533–1554. Processes which can be used to attach molecular receptor probes to surfaces using self-assembled nanolayers are described in Lenigk et al., *Surface Characterization of a Silicon-Chip-Based DNA Microarray*, Langmuir, 2001, pp. 2497–2501. The disclosures of both of these publications are hereby incorporated herein by reference in their entirety as if set forth fully herein, and need not be described further herein. Also, some polymers have shown affinity for nanoparticle adhesion, or can be chemically modified to have a strong affinity, which can be used as an anchor layer.

As shown in FIG. 1A, the thickness 110b of the insulating layer 110 may be used to control the spacing between the first electrode end 150a and the second electrode end 120a, so as to provide quantum mechanical tunneling therebetween through the at least one nanoparticle 140. Since the thickness 110b of the insulating layer 110 may be well-controlled on a nanometer scale using conventional microelectronic techniques, the desired spacing for a single-electron transistor may be obtained relatively inexpensively and/or with relatively high yields.

In embodiments shown in FIGS. 1A and 1B, the insulating layer end 110a is a continuous insulating layer end that surrounds the sidewall 150b. However, a discontinuous insulating layer end may be provided, as well. Moreover, in FIGS. 1A and 1B, the second electrode end 120a is illustrated as a continuous second electrode end that surrounds the continuous insulating layer end 110a. However, in other embodiments, a discontinuous second electrode end may be provided.

Thus, in FIGS. 1A and 1B, the continuous insulating layer end 110a and the continuous second electrode end 120a form first and second rings, respectively, that surround the first electrode end 150a. Moreover, in FIGS. 1A and 1B, the first and second rings are circular first and second rings.

Figure 1C:
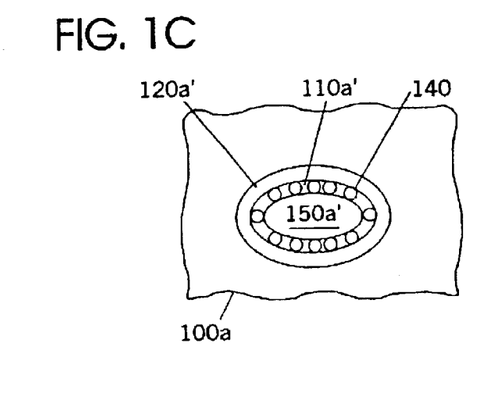
Figure 1D:
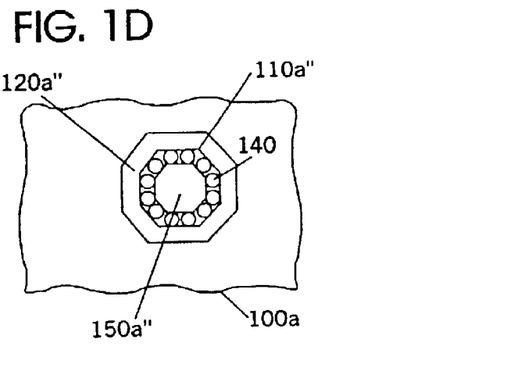
Figure 2A:
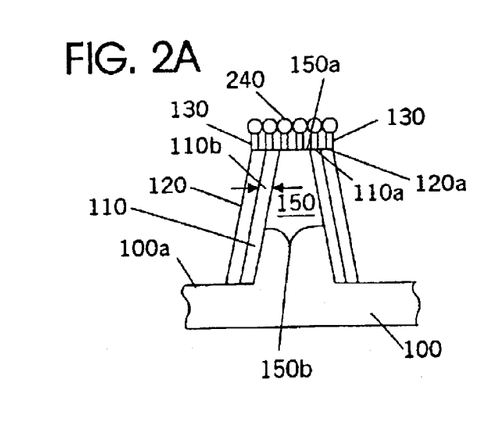
Figure 2B:
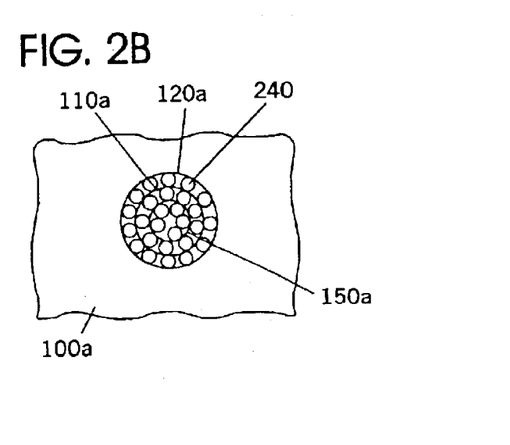
Figure 2C:
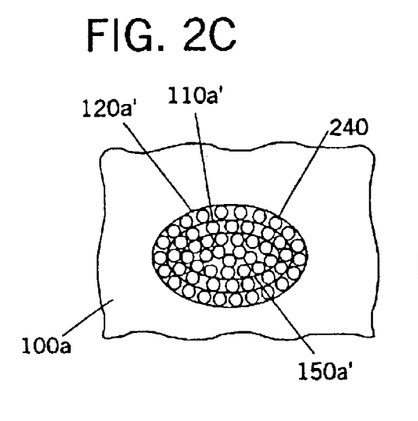
Figure 2D:
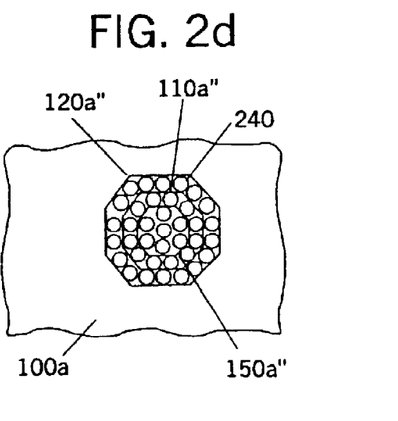

FIGS. 1C and 1D are top views of other embodiments of the present invention, wherein the first and second rings 110a and 120a of FIG. 1B are elliptical first and second rings 110a' and 120a', or polygonal first and second rings 110a" and 120a", respectively. The first electrode end may be an elliptical or polygonal first electrode end 150a' or 150a", respectively, as well. Moreover, in FIG. 1A, the first electrode end 150a, the insulating layer end 110a and the second electrode end 120a are coplanar. However, they need not be coplanar and they need not extend parallel to the substrate face 100.

From a dimensional standpoint, the first electrode end 150a, 150a', 150a" may have a diameter or longest dimension that is on the order of 100 nm. The insulating layer 110 may have thickness 110b that is between about 10 nm and about 20 nm, and the second electrode 120a, 120a', 120a" may have a thickness of between about 10 nm and about 20 nm. Functionally, the thickness 110b of the insulating layer 110 may be used to support quantum mechanical tunneling using the nanoparticles 140, whereas the size of the first and second electrodes 150 and 120 may vary over a wide range, based on many other considerations, such as a desired overall size for the single-electron transistor, structural soundness, etc.

The self-assembled monolayer 130 may maintain at least one nanoparticle 140 at a distance of about 1 nm from both the first electrode end 150a and from the second electrode end 120a. However, distances of between about 0.5 nm to about 5 nm also may be used in other embodiments. Other distances also may be used.

In embodiments of FIGS. 1A–1D, a plurality of nanoparticles 140 are provided on the insulating layer end 110a, whereas the first electrode ends 150a, 150a', 150a", and the second electrode ends 120a, 120a', 120a" are free of nanoparticles 140 thereon. However, in other embodiments of the invention, as shown in FIGS. 2A–2D, a plurality of nanoparticles 240 are provided on the insulating layer end 110a, 110a', 110a" on the first electrode end 150a, 150a', 150a", and on the second electrode end 120a, 120a', 120a". It also will be understood that the nanoparticles 240 may be provided on either the first electrode end 150a, 150a', 150a" or the second electrode end 120a, 120a', 120a". Moreover, the plurality of nanoparticles 240 may be randomly spaced and/or may be spaced in a linear and/or nonlinear, orthogonal and/or non-orthogonal array of equally and/or unequally (aperiodic and/or random) spaced apart nanoparticles. The nanoparticles 240 may have a predetermined relationship to the underlying layers and/or a random relationship thereto.

Figure 3:
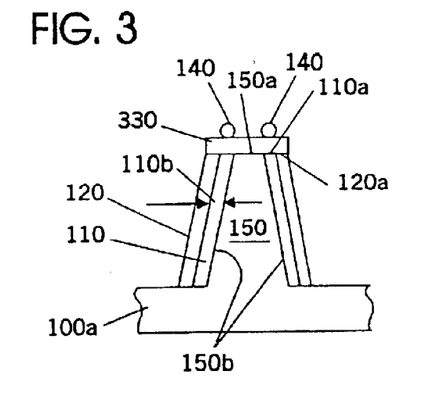
Figure 4:
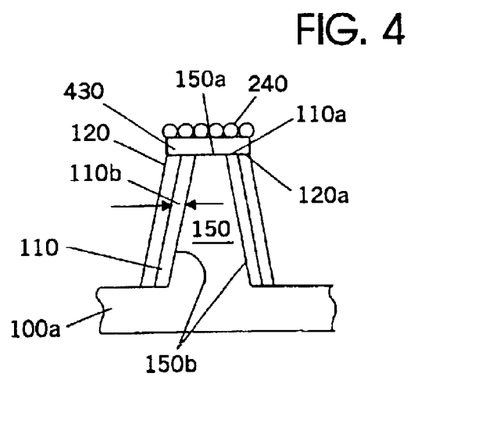

FIGS. 3 and 4 are cross-sectional views of single-electron transistors according to other embodiments of the invention. In these embodiments, an insulating layer or sublayers 330, 430, comprising silicon dioxide, silicon nitride and/or other conventional insulating layers, are provided between the at least one nanoparticle 140, 240, and the first electrode end 150a, the insulating layer end 110a and/or the second electrode end 120a. The use of an insulating layer to anchor a nanoparticle is described, for example in Andres et al., "*Coulomb Staircase" Single Electron Tunneling at Room Temperature in a Self Assembled Molecular Nanostructure*, Science, 1996, Vol. 272, pp. 1323–1325, the disclosure of which is hereby incorporated herein by reference in its entirety as if set forth fully herein, and need not be described further herein. It also will be understood that the insulating layer 330 may comprise a portion of the insulating layer 110. In yet other embodiments, both an insulating layer 330, 430 of FIGS. 3 and 4, and a self-assembled monolayer 130 of FIGS. 1 and 2 may be used in combination. Other intermediary layers also may be used.

Figure 5:
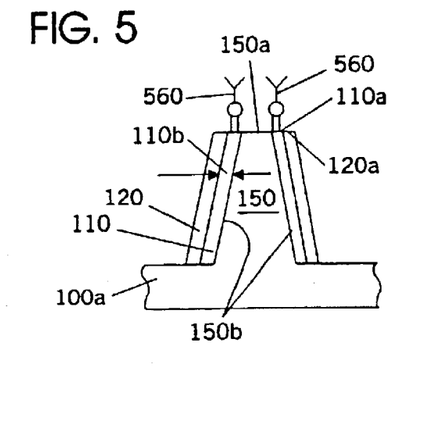

FIG. 5 is a cross-sectional view of yet other embodiments of the present invention, wherein an analyte-specific binding agent 560 is provided on a surface of the at least one nanoparticle 140, to provide a chemically-gated single electrode transistor. An analyte-specific binding agent 560 of FIG. 5 also may be provided on any of the embodiments that were described in connection with any of the preceding figures, to provide a chemically-gated single-electron transistor. Analyte-specific binding agents are described, for example in the above-incorporated Ulman, Lenigk et al., Feldheim et al. and Brousseau et al. publications, and need not be described further herein.

Figure 6:
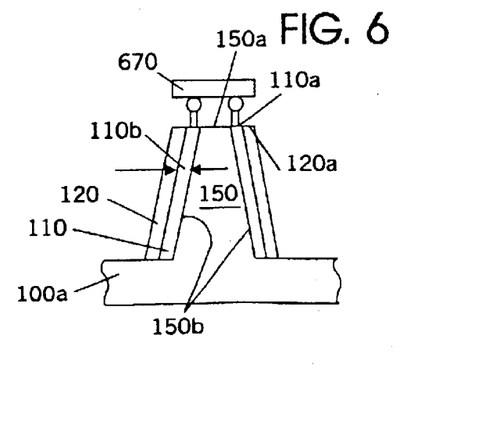

FIG. 6 is a cross-sectional view of other embodiments of the present invention, wherein a gate electrode 670 is provided on the at least one nanoparticle 140 opposite the insulating layer end 110a, to provide a single-electron field effect transistor. Single layer and/or multilayer gate electrodes may be provided. A gate electrode also may be provided in any of the embodiments that are described in connection with any of the figures herein. An insulating layer also may be provided between the gate electrode 670 and the at least one nanoparticle, to provide an insulated gate electrode.

Figure 7:
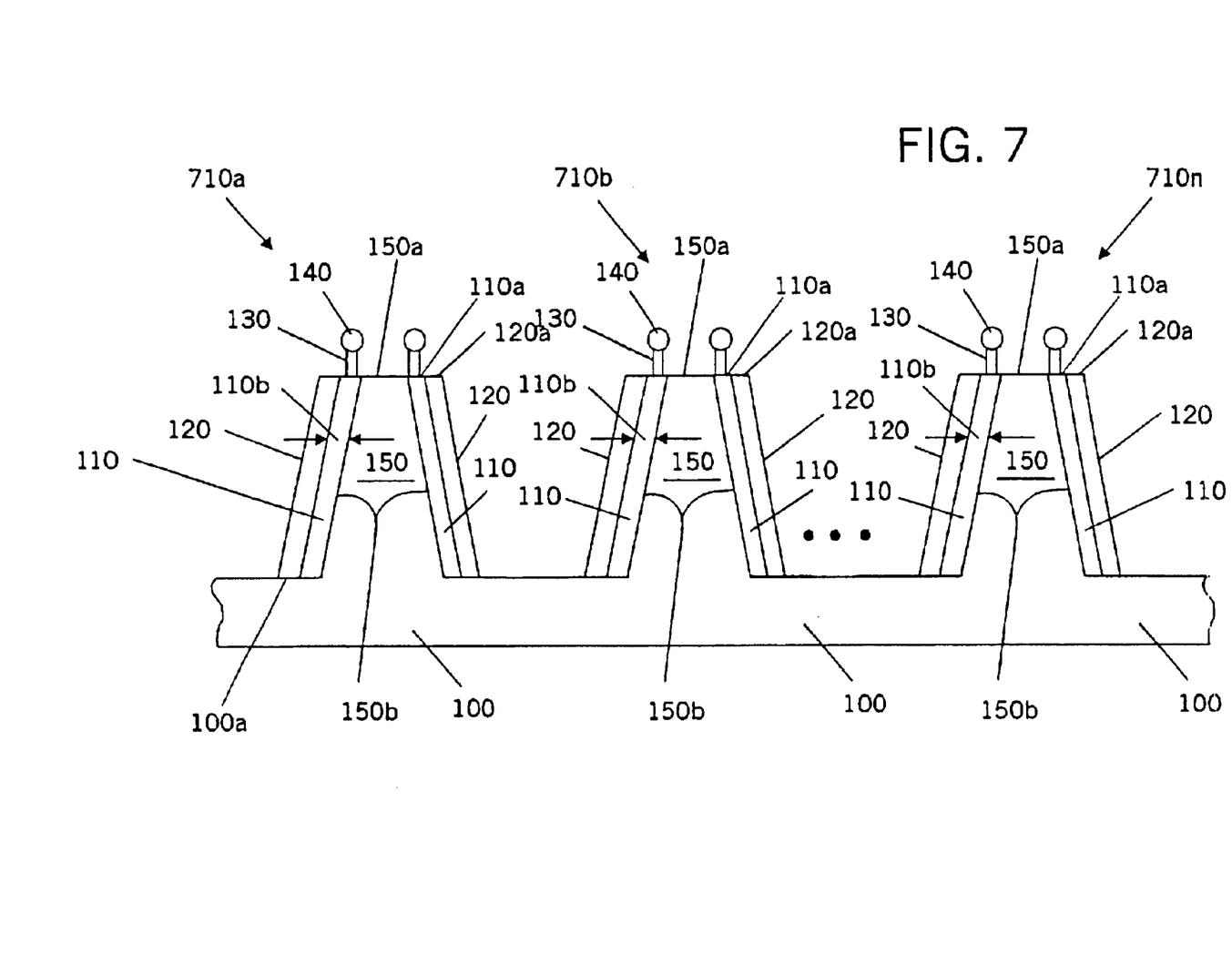

In all of the above-described embodiments, only one single-electron transistor is illustrated on a substrate. However, as illustrated in FIG. 7, an array of single-electron transistors 710a–710n may be provided on a substrate. One- and/or two-dimensional, linear and/or nonlinear, orthogonal and/or nonorthogonal arrays may be provided, with the spacing among the single-electron transistors being equal (periodic) and/or unequal (aperiodic and/or random). Each single-electron transistor 710a–710n may be identical, or at least some of the single-electron transistors may be dissimilar. Moreover, any of the embodiments of the figures herein may be used for any of the single-electron transistors 710a–710n. Finally, in these embodiments, the insulating layers 110 of some or all of the array of single-electron transistors 710a-710n may comprise portions of a single insulating layer. Moreover, the second electrodes 120 of some or all of the single-electron-transistors 710a–710n may comprise portions of a single conductive layer.

Figure 8:
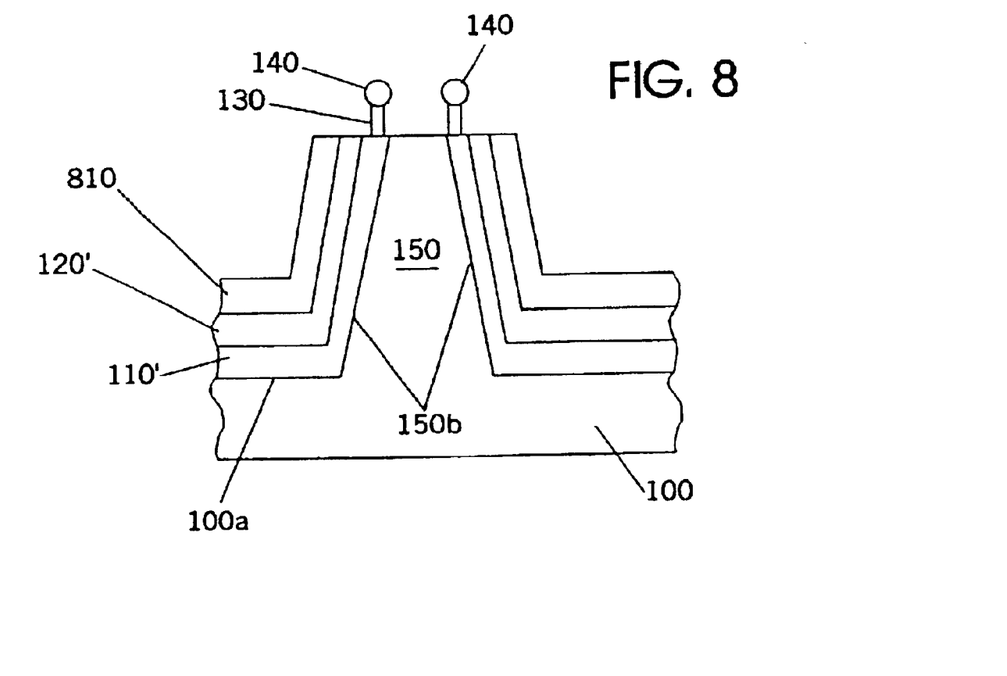

FIG. 8 is a cross-sectional view of yet other embodiments of the present invention that include extended insulating layers and/or electrodes. In particular, in FIG. 8, the insulating layer 110' and the second electrode 120' both extend along the substrate face 100a, in addition to extending along the first electrode sidewall 150b. It also will be understood that only one of the insulating layer 110' or the second electrode 120' may extend along the substrate face 100a. Any of the configurations that are described in connection with any of the figures herein may be combined with the extended insulating layer 110' and/or extended second electrode 120' of FIG. 8.

Still referring to FIG. 8, a second insulating layer 810 also may be provided on the second electrode 120' opposite the insulating layer 110'. The second insulating layer 810 may comprise a layer or multiple sublayers comprising silicon dioxide, silicon nitride one or more self-assembled monolayers, one or more polymer films and/or other materials that may be used to protect a device from an outside (ambient) environment. The second insulating layer 810 may be a specialized layer that may depend upon the ambient in which a chemically-gated single-electron transistor is being used. The second insulating layer 810 may be used with or without the extended layers 110' and 120' of FIG. 8, and/or with any other embodiments that are described in connection with any of the figures herein.

Figure 9:
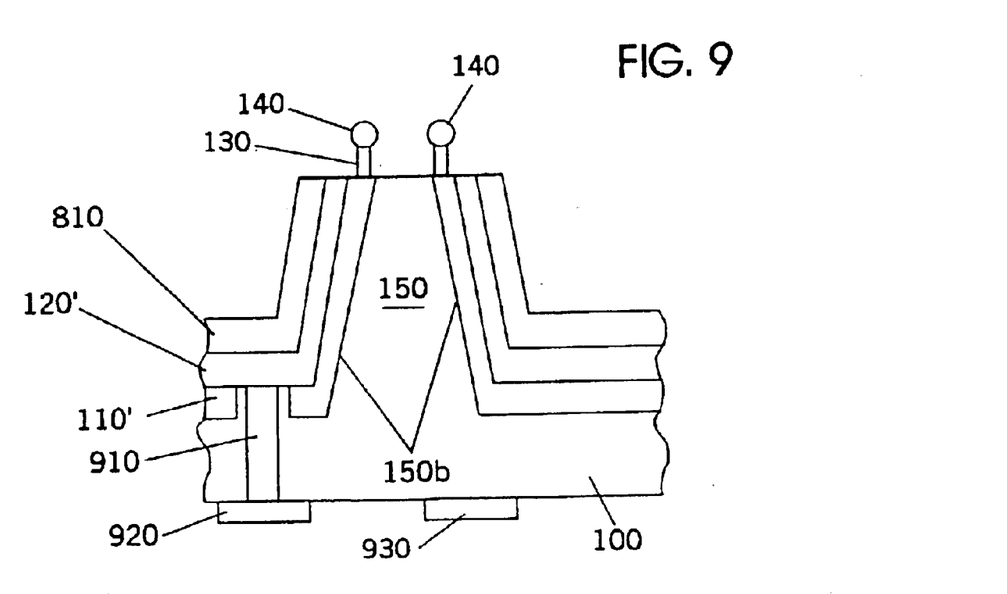

FIG. 9 is a cross-sectional view of other embodiments of the present invention. In FIG. 9, external electrical contacts are provided using a conductive via 910 that electrically connects the second electrode 120' to a pad 920 on the back face of the substrate 100. The first electrode 150 also may contact the back face of the substrate 100 at a second pad 930 using internal doped regions of the substrate and/or other conventional techniques. Appropriate insulating regions may be provided to electrically insulate the first and second pads 920 and 930 from one another and/or to insulate the conductive via 910 from other regions, using techniques well known to those having skill in the art. Solder bumps and/or other interconnect techniques may be used to electrically and/or mechanically connect the first and second contact pads 920 and 930 to an external device. These and other external contact schemes also may be used with any of the described embodiments of the invention.

FIGS. 10A–10F are cross-sectional views of single-electron transistors according to embodiments of the present invention, during intermediate fabrication steps according to embodiments of the present invention. These method embodiments may be used to fabricate single-electron transistors as illustrated in FIG. 1A. However, similar method embodiments may be used to fabricate single-electron transistors of FIGS. 1B–9 and/or combinations thereof.

Figure 10A:
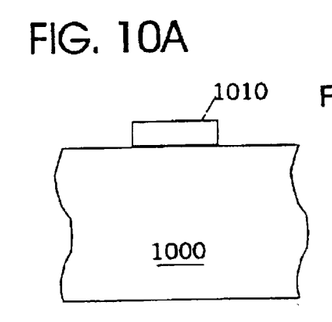
FIGS. 10A–10F and 11A–11I are side cross-sectional views of single-electron transistors according to embodiments of the present invention, during intermediate fabrication steps according to embodiments of the present invention.

Referring now to FIG. 10A, a mask region 1010 is formed on a substrate 1000, for example by forming a conventional mask comprising silicon nitride on a conventional substrate, and then patterning using conventional photolithography. It will be understood that since the width of the mask region 1010 need not determine the spacing between the first and second electrodes that are formed subsequently, conventional photolithography may be used. It also will be understood that the substrate 1000 may be a conventional substrate, as was described in connection with FIG. 1A, such as a layer of doped polysilicon and/or other conductive material on a monocrystalline silicon substrate.

Figure 10B:
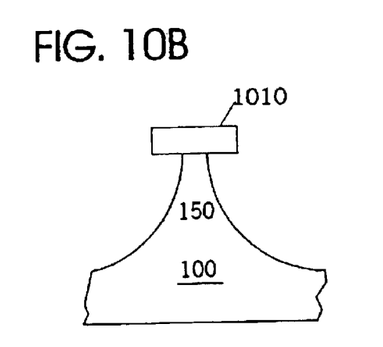

Then, referring to FIG. 10B, an anisotropic (wet) etch may be performed using the masking region 1010 as an etching mask, to form the first electrode 150 on a substrate 100. Other conventional etching techniques and/or other conventional post-forming techniques such as selective epitaxial growth, may be used.

Figure 10C:
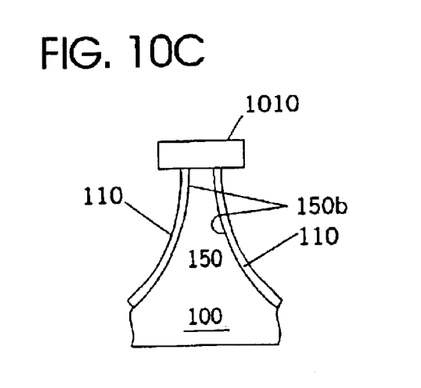

Referring now to FIG. 10C, the insulating layer 110 is formed, for example by performing a conformal deposition, for example using Chemical Vapor Deposition (CVD), such as Plasma-Enhanced Chemical Vapor Deposition (PECVD), which may not form a continuous insulating layer on the mask region. It also will be understood that the insulating layer 110 also may be formed on the mask region 1010.

Figure 10D:
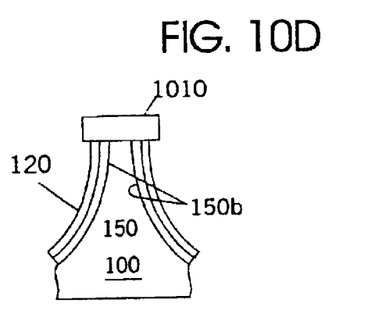

Then, referring to FIG. 10D, the second electrode 120 is formed on the insulating layer 110, for example using a directional (angled) deposition technique, which may not form a continuous layer on the mask region 1010.

Alternatively, other deposition techniques may be performed which may also form a conformal layer on the mask region 1010.

Figure 10E:
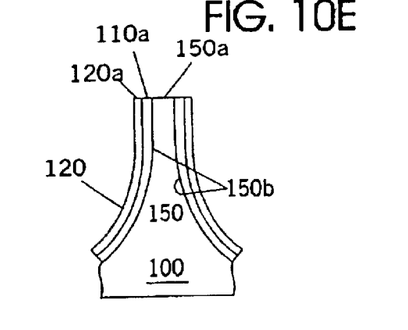

Then, referring to FIG. 10E, the mask region 1010 is removed, which may also remove any portions of the insulating layer 110 and/or the second electrode 120 thereon, to thereby define the first electrode end 150a, the insulating layer end 110a, and the second electrode end 120a.

Figure 10F:
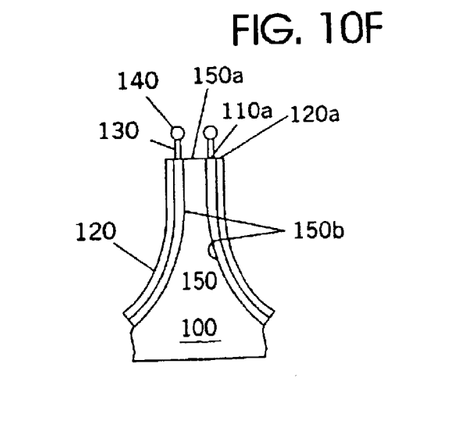

Referring now to FIG. 10F, absorption of the anchoring self-assembled monolayer 130 may be performed, for example, using techniques that were described above. At least one nanoparticle 140 then is attached to the anchoring self-assembled monolayer 130, for example, using techniques that were described above.

Figure 11A:
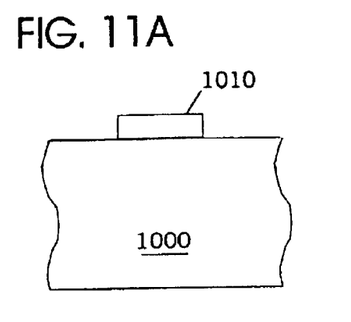
Figure 11B:
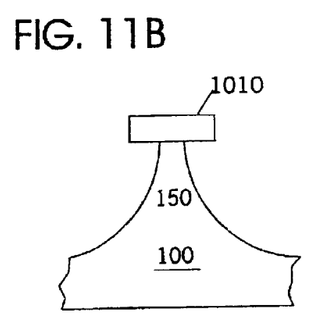
Figure 11C:
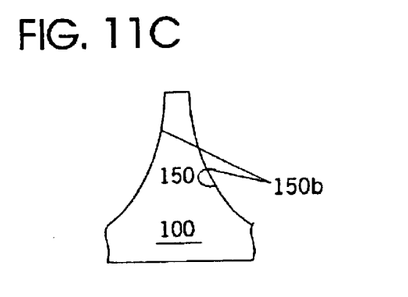
Figure 11D:
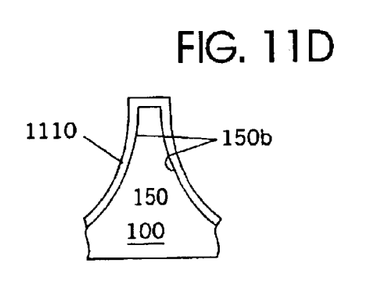
Figure 11E:
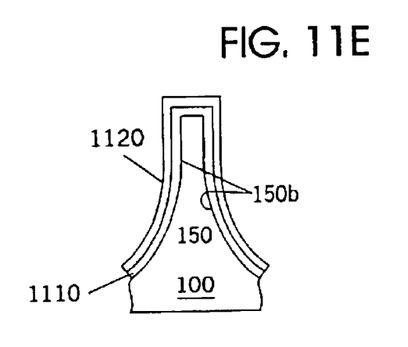

FIGS. 11A–11I are cross-sectional views of other single-electron transistors according to embodiments of the present invention, during intermediate fabrication steps according to embodiments of the present invention. As shown in FIG. 11A, a mask region 1010 is formed on a substrate, similar to FIG. 10A. As shown in FIG. 11B, anisotropic etching and/or other techniques are used to create a first (post) electrode 150, similar to FIG. 10B. As shown in FIG. 11C, the masking region 1010 then is removed. In FIG. 11D, a conformal insulating layer 1110 is formed on the first electrode 150, for example, using conventional conformal deposition techniques. In other embodiments, directional deposition may need not be used. As shown in FIG. 11E, a conformal second conductive layer 1120 is formed on the conformal insulating layer 1110, for example using conventional conformal deposition techniques. In other embodiments, directional deposition may not need to be used. Layers 1110 and 1120 may comprise materials that were described earlier for layers 110 and 120, respectively.

Figure 11F:
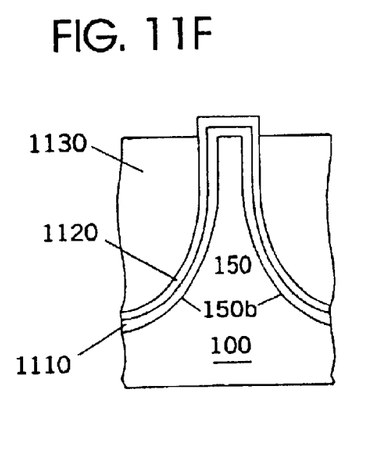

Referring now to FIG. 11F, a recessed layer 1130 then may be formed between structures of FIG. 11B. The recessed layer 1130 may include one or more sublayers comprising silicon dioxide, silicon nitride, polyimide and/or other materials that are compatible with a subsequent selective etching and/or chemical-mechanical polishing process. The recessed layer 1130 may be recessed from the top of the conductive layer 1120 by at least the thickness of layers 1110 and 1120. However, smaller or larger recesses also may be provided.

Figure 11G:
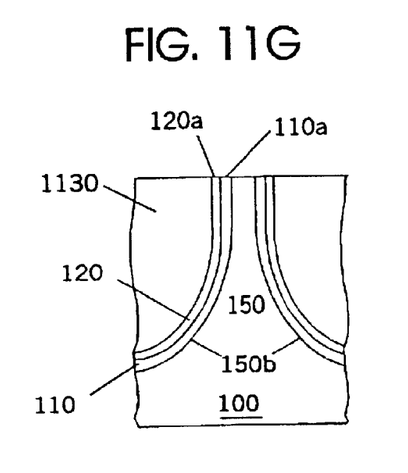
Figure 11H:
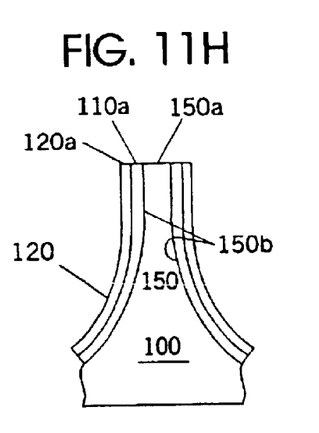
Figure 11I:
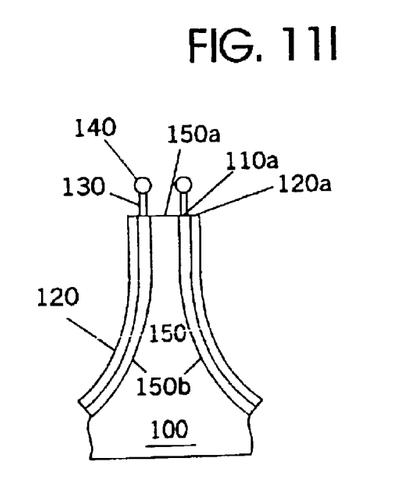

Referring now to FIG. 11G, chemical-mechanical polishing and/or other conventional techniques are used to planarize the structure, and thereby define the insulating layer 110 including the insulating layer end 110a, and the second electrode 120 including the second electrode end 120a. Referring now to FIG. 11H, the recessed layer 1130 is removed using conventional techniques, to provide a structure similar to FIG. 10E. Finally, at FIG. 11I, at least one nanoparticle 140 and an optional self-aligned monolayer 130 are formed as was described in connection with FIG. 10F.

Accordingly, embodiments of the present invention can provide arrays, including large arrays, of dual concentric electrodes. A conducting center electrode and an outer ring electrode can allow electrochemical reactions to be monitored at the apexes of each electrode-insulator-electrode tower. The electrodes may be derivatized to include chemical specificity to reactions taking place at the surfaces. Enhanced sensitivity can be made possible by attaching nanometer-sized colloidal particles to the insulating regions between the electrodes, which can create single-electron transistors. The colloids can be functionalized with chemically-specific receptors and/or molecules, to incorporate specificity to these reactions.

Single-electron transistors or arrays thereof, according to embodiments of the invention, may be used, for example, as sensing platforms in the wells of microtiter plates, for biological assays. Their enhanced sensitivity compared to conventional larger electrodes can benefit drug discovery and/or biochemistry. Their small size also can afford direct insertion of the arrays into living cells, which can allow in vivo chemical study and/or direct mapping of chemical pathways and/or concentrations within the cells.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of fabricating a single-electron transistor comprising:

forming a mask region on a substrate;

anisotropically etching the substrate with the mask region thereon, to form a first electrode on the substrate having a first electrode end, with the mask region on the first electrode end;

conformally forming an insulating layer on at least a portion of the first electrode;

conformally forming a second electrode on at least a portion of the insulating layer opposite the first electrode; and placing at least one nanoparticle on the insulating layer, between the first electrode and the second electrode.

2. A method according to claim 1:

wherein the conformally forming an insulating layer comprises conformally forming an insulator on the first electrode except for on the first electrode end that has the mask region thereon; and wherein the conformally forming a second electrode comprises conformally forming a second electrode on the insulating layer but not on the first electrode end that has the mask region thereon.

3. A method according to claim 2 wherein the following is performed between the conformally forming a second electrode and the placing a nanoparticle:

removing the mask region from the first electrode end.

4. A method according to claim 3 wherein the placing a nanoparticle comprises placing a nanoparticle on the insulating layer, adjacent the first electrode end.

5. A method according to claim 1 wherein the following is performed between the conformally forming a second electrode and the placing at least one nanoparticle:

removing the second electrode and the insulating layer from the first electrode end.

6. A method according to claim 5 wherein the placing a nanoparticle comprises placing a nanoparticle on the insulating layer, adjacent the first electrode end.

7. A method according to claim 5 wherein the removing comprises:

forming a recessed layer on the substrate such that the first electrode end, the insulating layer on the first electrode end and the second electrode on the first electrode end protrude from the recessed layer; and planarizing the first electrode end, the insulating layer on the first electrode end and the second electrode on the first electrode end that protrude from the recessed layer.

8. A method according to claim 1 wherein the insulating layer is less than about 20 nm thick.

9. A method according to claim 8 wherein the insulating layer is about 10 nm thick.

10. A method according to claim 1 wherein the placing comprises placing a plurality of nanoparticles on the insulating layer, between the first electrode and the second electrode, wherein the first electrode and the second electrode are free of nanoparticles thereon.

11. A method according to claim 1 wherein the placing comprises placing a plurality of nanoparticles on the insulating layer, between the first electrode and the second electrode, on the first electrode and on the second electrode.

12. A method according to claim 1 further comprising:
forming an analyte-specific binding agent on a surface of the at least one nanoparticle to provide a chemically-gated single-electron transistor.

13. A method according to claim 1 further comprising:
forming a gate electrode on the at least one nanoparticle opposite the insulating layer to provide a single-electron field effect transistor.

14. A method according to claim 1 further comprising forming a second insulating layer on the second electrode, opposite the insulating layer.

15. A method of fabricating a single-electron transistor comprising:
forming a first electrode on a substrate;
conformally forming an insulating layer on at least a portion of the first electrode;
conformally forming a second electrode on at least a portion of the insulating layer opposite the first electrode;
forming a self-assembled monolayer on the insulating layer, between the first electrode and the second electrode; and
placing at least one nanoparticle on the self-assembled monolayer, opposite the insulating layer.

16. A method according to claim 15:
wherein the following is performed between the conformally forming a second electrode and the forming a self-assembled monolayer:
forming a second insulating layer on the insulating layer; and
wherein the forming a self-assembled monolayer comprises forming a self-assembled monolayer on the second insulating layer, opposite the insulating layer.

17. A method of fabricating a single-electron transistor comprising:

forming first and second electrodes and an insulating layer therebetween on a substrate, such that the thickness of the insulating layer defines a spacing between the first and second electrodes;
forming a self-assembled monolayer on the insulating layer, between the first electrode and the second electrode; and
placing at least one nanoparticle on the self-assembled monolayer, opposite the insulating layer.

18. A method according to claim 17 wherein the insulating layer is less than about 20 nm thick.

19. A method according to claim 18 wherein the insulating layer is about 10 nm thick.

20. A method according to claim 17 wherein the placing comprises placing a plurality of nanoparticles on the insulating layer, between the first electrode and the second electrode, wherein the first electrode and the second electrode are free of nanoparticles thereon.

21. A method according to claim 17 wherein the placing comprises placing a plurality of nanoparticles on the insulating layer, between the first electrode and the second electrode, on the first electrode and on the second electrode.

22. A method according to claim 17:
wherein the following is performed between the forming first and second electrodes and an insulating layer therebetween and the forming a self-assembled monolayer:
forming a second insulating layer on the insulating layer; and
wherein the forming a self-assembled monolayer comprises forming a self-assembled monolayer on the second insulating layer, opposite the insulating layer.

23. A method according to claim 17 further comprising:
forming an analyte-specific binding agent on a surface of the at least one nanoparticle to provide a chemically-gated single-electron transistor.

24. A method according to claim 17 further comprising:
forming a gate electrode on the at least one nanoparticle opposite the insulating layer to provide a single-electron field effect transistor.

25. A method according to claim 17 further comprising forming a second insulating layer on the second electrode, opposite the insulating layer.

* * * * *